(12) United States Patent
Reed

(10) Patent No.: US 9,526,498 B2
(45) Date of Patent: Dec. 27, 2016

(54) SURGICAL DEVICE WITH A TRIGGER LOCKOUT MECHANISM DEVICE

(71) Applicant: Covidien LP, Mansfield, MA (US)

(72) Inventor: Scott W. Reed, Winsted, CT (US)

(73) Assignee: Covidien LP, Mansfield, MA (US)

( * ) Notice: Subject to any disclaimer, the term of this patent is extended or adjusted under 35 U.S.C. 154(b) by 294 days.

(21) Appl. No.: 14/310,266

(22) Filed: Jun. 20, 2014

(65) Prior Publication Data

US 2015/0080911 A1 Mar. 19, 2015

Related U.S. Application Data

(60) Provisional application No. 61/878,924, filed on Sep. 17, 2013.

(51) Int. Cl.
*A61B 17/10* (2006.01)
*A61B 17/068* (2006.01)
(Continued)

(52) U.S. Cl.
CPC .......... *A61B 17/068* (2013.01); *A61B 17/1285* (2013.01); *A61B 2017/00367* (2013.01);
(Continued)

(58) Field of Classification Search
CPC ..................... A61B 17/068; A61B 2017/2923; A61B 17/064; A61B 17/0644; A61B 17/0682; A61B 17/105; A61B 17/1285; A61B 2017/00367; A61B 2017/2946
(Continued)

(56) References Cited

U.S. PATENT DOCUMENTS 3,866,510 A 2/1975 Eibes et al.
4,884,572 A 12/1989 Bays et al.
(Continued)

FOREIGN PATENT DOCUMENTS

DE 10300787 A1 9/2004
DE 10 2010 015009 A1 10/2011
(Continued)

OTHER PUBLICATIONS

Extended European Search report corresponding to counterpart Int'l Appication No. EP 14 18 1900.3, dated Apr. 9, 2015.
(Continued)

*Primary Examiner* — Katherine M Shi

(57) ABSTRACT

A surgical device includes a handle assembly, a drive assembly, and a lockout mechanism. The handle assembly includes a fixed handle and a moveable handle. The moveable handle includes an internal end defining an opening. The opening includes a toothed rack. The moveable handle has an initial position and a full-squeezed position. In the initial position, the moveable handle is spaced-apart from the fixed handle. In the full-squeezed position, the moveable handle is approximated toward the fixed handle. The drive assembly is disposed within the handle assembly and is engaged by the toothed rack. The lockout mechanism is disposed with in the handle assembly and is engaged with the moveable handle to prevent movement of the moveable handle towards the initial position before the moveable handle reaches the full-squeezed position.

14 Claims, 13 Drawing Sheets

(51) Int. Cl.
    *A61B 17/128* (2006.01)
    *A61B 17/00* (2006.01)
    *A61B 17/29* (2006.01)

(52) U.S. Cl.
    CPC .............. *A61B 2017/2903* (2013.01); *A61B 2017/2923* (2013.01); *A61B 2090/08021* (2016.02)

(58) Field of Classification Search
    USPC ................. 606/139, 142; 227/175.1–182.1
    See application file for complete search history.

(56) References Cited

U.S. PATENT DOCUMENTS

| | | | |
|---|---|---|---|
| 5,085,661 A | 2/1992 | Moss | |
| 5,171,247 A | 12/1992 | Hughett et al. | |
| 5,171,249 A | 12/1992 | Stefanchik et al. | |
| 5,176,306 A | 1/1993 | Heimerl et al. | |
| 5,207,697 A | 5/1993 | Carusillo et al. | |
| 5,228,256 A | 7/1993 | Dreveny | |
| 5,236,563 A | 8/1993 | Loh | |
| 5,246,441 A | 9/1993 | Ross et al. | |
| 5,246,450 A | 9/1993 | Thornton et al. | |
| 5,312,023 A | 5/1994 | Green et al. | |
| 5,330,487 A | 7/1994 | Thornton et al. | |
| 5,344,061 A | 9/1994 | Crainich | |
| 5,356,064 A | 10/1994 | Green et al. | |
| 5,382,254 A | 1/1995 | McGarry et al. | |
| 5,398,861 A | 3/1995 | Green | |
| 5,403,327 A | 4/1995 | Thornton et al. | |
| 5,433,721 A | 7/1995 | Hooven et al. | |
| 5,439,468 A | 8/1995 | Schulze et al. | |
| 5,466,243 A | 11/1995 | Schmieding et al. | |
| 5,467,911 A | 11/1995 | Tsuruta et al. | |
| 5,474,566 A | 12/1995 | Alesi et al. | |
| 5,474,567 A | 12/1995 | Stefanchik et al. | |
| 5,522,844 A | 6/1996 | Johnson | |
| 5,527,319 A | 6/1996 | Green et al. | |
| 5,553,765 A | 9/1996 | Knodel et al. | |
| 5,562,685 A | 10/1996 | Mollenauer et al. | |
| 5,564,615 A | 10/1996 | Bishop et al. | |
| 5,582,615 A | 12/1996 | Foshee et al. | |
| 5,582,616 A | 12/1996 | Bolduc et al. | |
| 5,584,425 A | 12/1996 | Savage et al. | |
| 5,588,581 A | 12/1996 | Conlon et al. | |
| 5,601,571 A | 2/1997 | Moss | |
| 5,601,573 A | 2/1997 | Fogelberg et al. | |
| 5,626,613 A | 5/1997 | Schmieding | |
| 5,628,752 A | 5/1997 | Asnis et al. | |
| 5,649,931 A | 7/1997 | Bryant et al. | |
| 5,662,662 A | 9/1997 | Bishop et al. | |
| 5,681,330 A | 10/1997 | Hughett et al. | |
| 5,683,401 A | 11/1997 | Schmieding et al. | |
| 5,685,474 A | 11/1997 | Seeber | |
| 5,697,935 A | 12/1997 | Moran et al. | |
| 5,709,692 A | 1/1998 | Mollenauer et al. | |
| 5,730,744 A | 3/1998 | Justin et al. | |
| 5,732,806 A | 3/1998 | Foshee et al. | |
| 5,735,854 A | 4/1998 | Caron et al. | |
| 5,741,268 A | 4/1998 | Schutz | |
| 5,762,255 A | 6/1998 | Chrisman et al. | |
| 5,782,844 A | 7/1998 | Yoon et al. | |
| 5,810,882 A | 9/1998 | Bolduc et al. | |
| 5,824,008 A | 10/1998 | Bolduc et al. | |
| 5,830,221 A | 11/1998 | Stein et al. | |
| 5,843,087 A | 12/1998 | Jensen et al. | |
| 5,897,564 A | 4/1999 | Schulze et al. | |
| 5,904,693 A | 5/1999 | Dicesare et al. | |
| 5,910,105 A | 6/1999 | Swain et al. | |
| 5,911,722 A | 6/1999 | Adler et al. | |
| 5,928,244 A | 7/1999 | Tovey et al. | |
| 5,928,252 A | 7/1999 | Steadman et al. | |
| 5,931,844 A | 8/1999 | Thompson et al. | |
| 5,941,439 A | 8/1999 | Kammerer et al. | |
| 5,954,259 A | 9/1999 | Viola et al. | |
| 5,961,524 A | 10/1999 | Crombie | |
| 5,964,772 A | 10/1999 | Bolduc et al. | |
| 5,976,160 A | 11/1999 | Crainich | |
| 5,997,552 A | 12/1999 | Person et al. | |
| 6,010,513 A | 1/2000 | Tormala et al. | |
| 6,013,991 A | 1/2000 | Philipp | |
| 6,039,753 A | 3/2000 | Meislin | |
| 6,074,395 A | 6/2000 | Trott et al. | |
| 6,099,537 A | 8/2000 | Sugai et al. | |
| 6,126,670 A | 10/2000 | Walker et al. | |
| 6,132,435 A | 10/2000 | Young | |
| 6,146,387 A | 11/2000 | Trott et al. | |
| 6,183,479 B1 | 2/2001 | Tormala et al. | |
| 6,228,098 B1 | 5/2001 | Kayan et al. | |
| 6,235,058 B1 | 5/2001 | Huene | |
| 6,241,736 B1 | 6/2001 | Sater et al. | |
| 6,261,302 B1 | 7/2001 | Voegele et al. | |
| 6,296,656 B1 | 10/2001 | Bolduc et al. | |
| 6,330,964 B1 | 12/2001 | Kayan et al. | |
| 6,387,113 B1 | 5/2002 | Hawkins et al. | |
| 6,402,757 B1 | 6/2002 | Moore, III et al. | |
| 6,425,900 B1 | 7/2002 | Knodel et al. | |
| 6,439,446 B1 | 8/2002 | Perry et al. | |
| 6,440,136 B1 | 8/2002 | Gambale et al. | |
| 6,450,391 B1 | 9/2002 | Kayan et al. | |
| 6,457,625 B1 | 10/2002 | Tormala et al. | |
| 6,551,333 B2 | 4/2003 | Kuhns et al. | |
| 6,562,051 B1 | 5/2003 | Bolduc et al. | |
| 6,572,626 B1 | 6/2003 | Knodel et al. | |
| 6,589,249 B2 | 7/2003 | Sater et al. | |
| 6,592,593 B1 | 7/2003 | Parodi et al. | |
| 6,626,916 B1 | 9/2003 | Yeung et al. | |
| 6,632,228 B2 | 10/2003 | Fortier et al. | |
| 6,652,538 B2 | 11/2003 | Kayan et al. | |
| 6,663,656 B2 | 12/2003 | Schmieding et al. | |
| 6,666,854 B1 | 12/2003 | Lange | |
| 6,695,867 B2 | 2/2004 | Ginn et al. | |
| 6,733,506 B1 | 5/2004 | McDevitt et al. | |
| 6,743,240 B2 | 6/2004 | Smith et al. | |
| 6,749,621 B2 | 6/2004 | Pantages et al. | |
| 6,755,836 B1 | 6/2004 | Lewis | |
| 6,773,438 B1 | 8/2004 | Knodel et al. | |
| 6,800,081 B2 | 10/2004 | Parodi | |
| 6,824,548 B2 | 11/2004 | Smith et al. | |
| 6,837,893 B2 | 1/2005 | Miller | |
| 6,840,943 B2 | 1/2005 | Kennefick et al. | |
| 6,843,794 B2 | 1/2005 | Sixto, Jr. et al. | |
| 6,869,435 B2 | 3/2005 | Blake, III | |
| 6,884,248 B2 | 4/2005 | Bolduc et al. | |
| 6,887,244 B1 | 5/2005 | Walker et al. | |
| 6,893,446 B2 | 5/2005 | Sater et al. | |
| 6,905,057 B2 | 6/2005 | Swayze et al. | |
| 6,929,661 B2 | 8/2005 | Bolduc et al. | |
| 6,942,674 B2 | 9/2005 | Belef et al. | |
| 6,945,979 B2 | 9/2005 | Kortenbach et al. | |
| 6,960,217 B2 | 11/2005 | Bolduc | |
| 6,966,919 B2 | 11/2005 | Sixto, Jr. et al. | |
| 6,988,650 B2 | 1/2006 | Schwemberger et al. | |
| 7,000,819 B2 | 2/2006 | Swayze et al. | |
| 7,128,254 B2 * | 10/2006 | Shelton, IV | A61B 17/07207 227/175.1 |
| 7,128,754 B2 | 10/2006 | Bolduc | |
| 7,204,847 B1 | 4/2007 | Gambale | |
| 7,261,716 B2 | 8/2007 | Strobel et al. | |
| 7,367,485 B2 | 5/2008 | Shelton, IV et al. | |
| 7,441,685 B1 | 10/2008 | Boudreaux | |
| 7,491,232 B2 | 2/2009 | Bolduc et al. | |
| 7,604,150 B2 | 10/2009 | Boudreaux | |
| 7,670,362 B2 | 3/2010 | Zergiebel | |
| 7,758,612 B2 | 7/2010 | Shipp | |
| 7,862,573 B2 | 1/2011 | Darois et al. | |
| 7,867,252 B2 | 1/2011 | Criscuolo et al. | |
| 7,931,660 B2 | 4/2011 | Aranyi et al. | |
| 8,002,811 B2 | 8/2011 | Corradi et al. | |
| 8,034,076 B2 | 10/2011 | Criscuolo et al. | |
| 8,075,570 B2 | 12/2011 | Bolduc et al. | |
| 8,087,142 B2 | 1/2012 | Levin et al. | |
| 8,114,099 B2 | 2/2012 | Shipp | |

(56) References Cited

U.S. PATENT DOCUMENTS

| | | | |
|---|---|---|---|
| 8,114,101 B2 | 2/2012 | Criscuolo et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,343,176 B2 | 1/2013 | Criscuolo et al. |
| 8,343,184 B2 | 1/2013 | Blier |
| 8,382,778 B2 | 2/2013 | Criscuolo et al. |
| 8,414,627 B2 | 4/2013 | Corradi et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,728,120 B2 | 5/2014 | Blier |
| 8,777,969 B2 | 7/2014 | Kayan |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 9,186,138 B2 | 11/2015 | Corradi et al. |
| 9,259,221 B2 | 2/2016 | Zergiebel |
| 2003/0009441 A1 | 1/2003 | Holsten et al. |
| 2003/0114839 A1 | 6/2003 | Looper et al. |
| 2004/0092937 A1 | 5/2004 | Criscuolo et al. |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0243139 A1 | 12/2004 | Lewis et al. |
| 2006/0129152 A1 | 6/2006 | Shipp |
| 2007/0038220 A1 | 2/2007 | Shipp |
| 2007/0162030 A1 | 7/2007 | Aranyi et al. |
| 2008/0097523 A1 | 4/2008 | Bolduc et al. |
| 2008/0147113 A1 | 6/2008 | Nobis et al. |
| 2008/0188868 A1 | 8/2008 | Weitzner et al. |
| 2008/0243106 A1 | 10/2008 | Coe et al. |
| 2008/0281336 A1 | 11/2008 | Zergiebel |
| 2008/0312687 A1 | 12/2008 | Blier |
| 2009/0118776 A1 | 5/2009 | Kelsch et al. |
| 2009/0188965 A1 | 7/2009 | Levin et al. |
| 2010/0030262 A1 | 2/2010 | McLean et al. |
| 2010/0270354 A1 | 10/2010 | Rimer et al. |
| 2010/0292710 A1 | 11/2010 | Daniel et al. |
| 2010/0292713 A1 | 11/2010 | Cohn et al. |
| 2010/0292715 A1 | 11/2010 | Nering et al. |
| 2011/0022065 A1 | 1/2011 | Shipp |
| 2011/0023358 A1 | 2/2011 | Marchildon |
| 2011/0060349 A1 | 3/2011 | Cheng et al. |
| 2011/0068148 A1 | 3/2011 | Hall et al. |
| 2011/0071578 A1 | 3/2011 | Colesanti et al. |
| 2011/0079627 A1 | 4/2011 | Cardinale et al. |
| 2011/0087240 A1 | 4/2011 | Shipp |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2013/0018392 A1 | 1/2013 | Zergiebel |
| 2013/0110088 A1 | 5/2013 | Wenchell |
| 2013/0131700 A1 | 5/2013 | Criscuolo et al. |
| 2013/0197591 A1 | 8/2013 | Corradi et al. |
| 2014/0114329 A1 | 4/2014 | Zergiebel |
| 2014/0121684 A1 | 5/2014 | Criscuolo et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |

FOREIGN PATENT DOCUMENTS

| | | |
|---|---|---|
| EP | 0374088 A1 | 6/1990 |
| EP | 0834280 A1 | 4/1998 |
| EP | 1273272 A2 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| JP | 09149906 | 6/1997 |
| WO | 00/16701 A1 | 3/2000 |
| WO | 02/34140 A2 | 5/2002 |
| WO | 03/034925 A2 | 5/2003 |
| WO | 03/103507 A2 | 12/2003 |
| WO | 2004/112841 A2 | 12/2004 |
| WO | 2005004727 A1 | 1/2005 |
| WO | 2009/039506 A1 | 3/2009 |
| WO | 2012/064692 A2 | 5/2012 |
| WO | 2013/046115 A1 | 4/2013 |

OTHER PUBLICATIONS

Extended European Search report corresponding to counterpart Int'l Appication No. EP 14 19 7885.8, dated Apr. 30, 2015.

Extended European Search Report corresponding to EP 14 15 8946.5, completed Jun. 20, 2014 and mailed Jul. 8, 2014; (9 pp).

Extended European Search Report corresponding to EP 14 17 8107.0, completed Nov. 24, 2014 and mailed Dec. 3, 2014; (5 pp).

Extended European Search Report corresponding to EP 14 17 4656.0, completed Jan. 16, 2015 and mailed Jan. 26, 2015; (7 pp).

Extended European Search Report corresponding to EP 14184907 completed Jan. 12, 2015 and mailed Jan. 27, 2015; (9 pp).

Extended European Search Report corresponding to EP No. 10 01 2659.8, completed Dec. 21, 2010 and mailed Jan. 3, 2011; 3 pages.

Extended European Search Report corresponding to EP No. 10 01 2646.5, completed Feb. 11, 2011 and mailed Feb. 22, 2011; 10 pages.

Extended European Search Report corresponding to EP No. 11 25 0549.0, completed Sep. 9, 2013 and mailed Sep. 17, 2013; 9 pages.

Extended European Search Report corresponding to EP 14 15 9394.7, completed Apr. 16, 2014 and mailed Apr. 29, 2014; 8 pages.

* cited by examiner

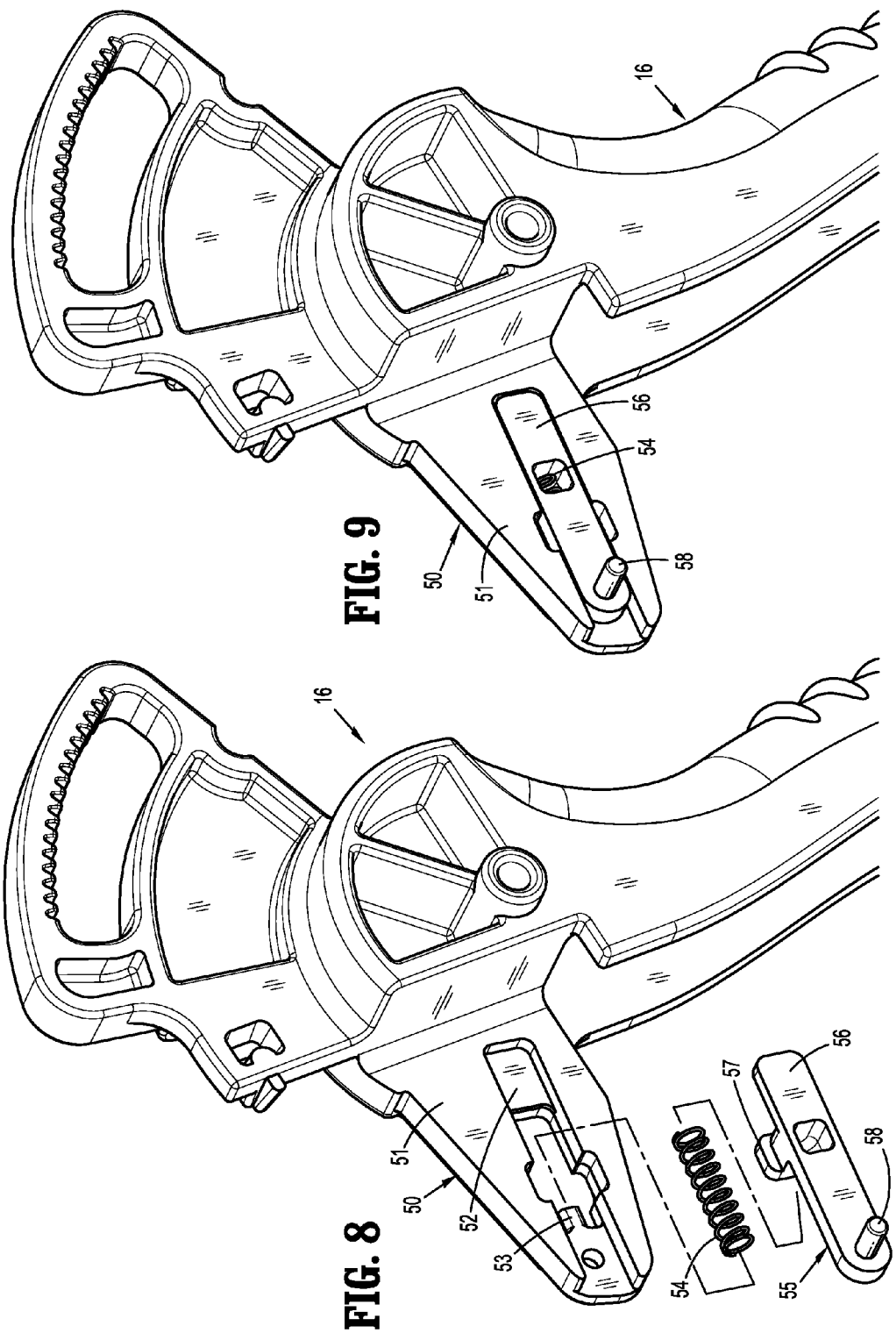

SURGICAL DEVICE WITH A TRIGGER LOCKOUT MECHANISM DEVICE

CROSS-REFERENCE TO RELATED APPLICATIONS

This application claims the benefit of and priority to U.S. Provisional Patent Application No. 61/878,924, filed Sep. 17, 2013, the entire disclosure of which is incorporated by reference herein.

BACKGROUND

1. Technical Field

The present disclosure relates to surgical devices, more specifically, to surgical devices that include a trigger lockout mechanism.

2. Background of Related Art

In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical devices therethrough using a trocar and for performing surgical procedures far removed from the incision.

During these procedures, the surgeon may be required to fire one or more surgical fasteners to join two portions of tissue, seal the end of a vessel, apply a surgical mesh to a target site, or to tack down body tissue. The surgeon will often apply multiple fasteners within the surgical site during the procedure. Surgical devices such as clip appliers, tack appliers, and staplers are known in the art for applying a single fastener during each entry to the body cavity.

Some surgical devices are able to apply multiple fasteners in endoscopic or laparoscopic procedures during a single entry into the body cavity. These surgical devices advance and/or form multiple fasteners during a single insertion into the body cavity. Generally, these surgical devices are configured to receive and cooperate with interchangeable fastener magazines to advance and form multiple fasteners during a single entry into a body cavity. One significant design goal is that the surgical device completely fires a single fastener and fully advances any remaining fasteners to a ready-to-fire position with each complete stroke of a trigger of the surgical device.

It is therefore desirable to improve the operation of surgical devices by providing an indication to the user of a firing of an individual fastener, the depletion of the fasteners contained in the magazine, or any other surgical event. It is also desirable to provide a surgical device that fully advances any remaining fasteners, a proper amount in the magazine, with each complete squeeze of a trigger of the surgical device.

SUMMARY

According to aspects of the present disclosure, a surgical device includes a handle assembly, an elongated member, an end effector, a drive assembly, and a lockout mechanism. The handle assembly including a fixed handle and a moveable handle. The moveable handle includes an internal end that defines an opening. The opening includes a toothed rack. In an initial position of the moveable handle, the moveable handle is spaced-apart from the fixed handle. In a full-squeezed position, the moveable handle is approximated toward the fixed handle. The elongated member extends from the handle assembly and defines a longitudinal axis. The end effector is positioned at a distal end of the elongated member. The drive assembly is disposed within the handle assembly. The toothed rack engages the drive assembly to transmit a rotative force to manipulate the end effector. The lockout mechanism is disposed within the handle assembly. The lockout mechanism engages the moveable handle to prevent movement of the moveable handle towards the initial position before the moveable handle reaches the full-squeezed position. In embodiments, the clutch is a roller clutch. In some embodiments, the clutch is a spring wrap clutch.

In aspects of the present disclosure, the lockout mechanism includes a wheel and a clutch. The wheel rotates in the first direction as the moveable handle is moved towards the full-squeezed position. The clutch engages the wheel. The clutch permits the wheel to rotate in the first direction and inhibits the wheel from rotating in a second direction opposite the first direction.

The lockout mechanism may include a slider having a pin and the wheel defines a plurality of slots. The plurality of slots of the wheel extend from the outer periphery of the wheel towards a center of the wheel. The pin engages one of the plurality of slots to rotate the wheel in the first direction when the moveable handle is moved towards the full-squeezed position. The pin is engaged by one of the plurality of slots to prevent the moveable handle from moving towards the initial position before the moveable handle reaches the full-squeezed position.

In aspects of the present disclosure, the surgical device includes a slider biasing member. The slider biasing member urges the slider such that the pin engages the periphery of the wheel. The pin sliding within one of the plurality of slots when the moveable handle is moved from the initial position to the full-squeezed position.

The handle assembly may include an integrally formed ramp. The ramp is positioned to move the pin against the slider biasing member from within one of the plurality of slots of the wheel when the moveable handle reaches the full-squeezed position.

In aspects of the present disclosure, the wheel includes a plurality of landings positioned about the periphery of the wheel. Each of the plurality of landings is positioned between a respective two of the plurality of slots. The pin engages one of the plurality of landings as the moveable handle returns from the full-squeezed position to the initial position.

In use, when the moveable handle returns to the initial position the pin may engage another of the plurality of slots adjacent to the one of the plurality of slots about the wheel.

According to another aspect of the present disclosure, a method for firing a surgical fastener from a surgical device includes the steps of providing a surgical device, engaging tissue with an end effector of the surgical device, and firing a first surgical fastener from the end effector. The end effector is loaded with at least one surgical fastener. Firing the first surgical fastener from the end effector includes moving the moveable handle from an initial position to a full-squeezed position. A toothed rack of the moveable handle engages a drive assembly to rotatably fire the first surgical fastener when the moveable handle reaches the full-squeezed position and when the moveable handle is released before reaching the full-squeezed position the lockout mechanism prevents movement of the moveable handle towards the initial position. In embodiments, the method includes firing a second fastener from the end effector by moving the movable handle through a complete stoke.

In some embodiments, the end effector includes a plurality of fasteners wherein the method includes the step of firing a fastener with each complete stroke of the moveable handle from the initial position to the full-squeezed position and each return of the moveable handle from the full-squeezed position to the initial position. The method may also include the step of advancing the plurality of fasteners within the end effector with each complete stroke of the movable handle.

In particular embodiments, the lockout mechanism includes a clutch and a wheel and the method includes the steps of permitting the wheel to rotate in a first direction and inhibiting the wheel from rotating in a second direction opposite the first direction when the clutch is engaged with the wheel. The wheel rotating in the first direction by moving the moveable handle from the initial position to the full-squeezed position.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 8 is a rear, perspective exploded view of a slider pin and a moveable handle shown in FIG. 7;

FIG. 9 is a rear, perspective view of the slider pin positioned on the movable handle of the surgical device of FIG. 1;

DETAILED DESCRIPTION OF EMBODIMENTS

Figure 1:
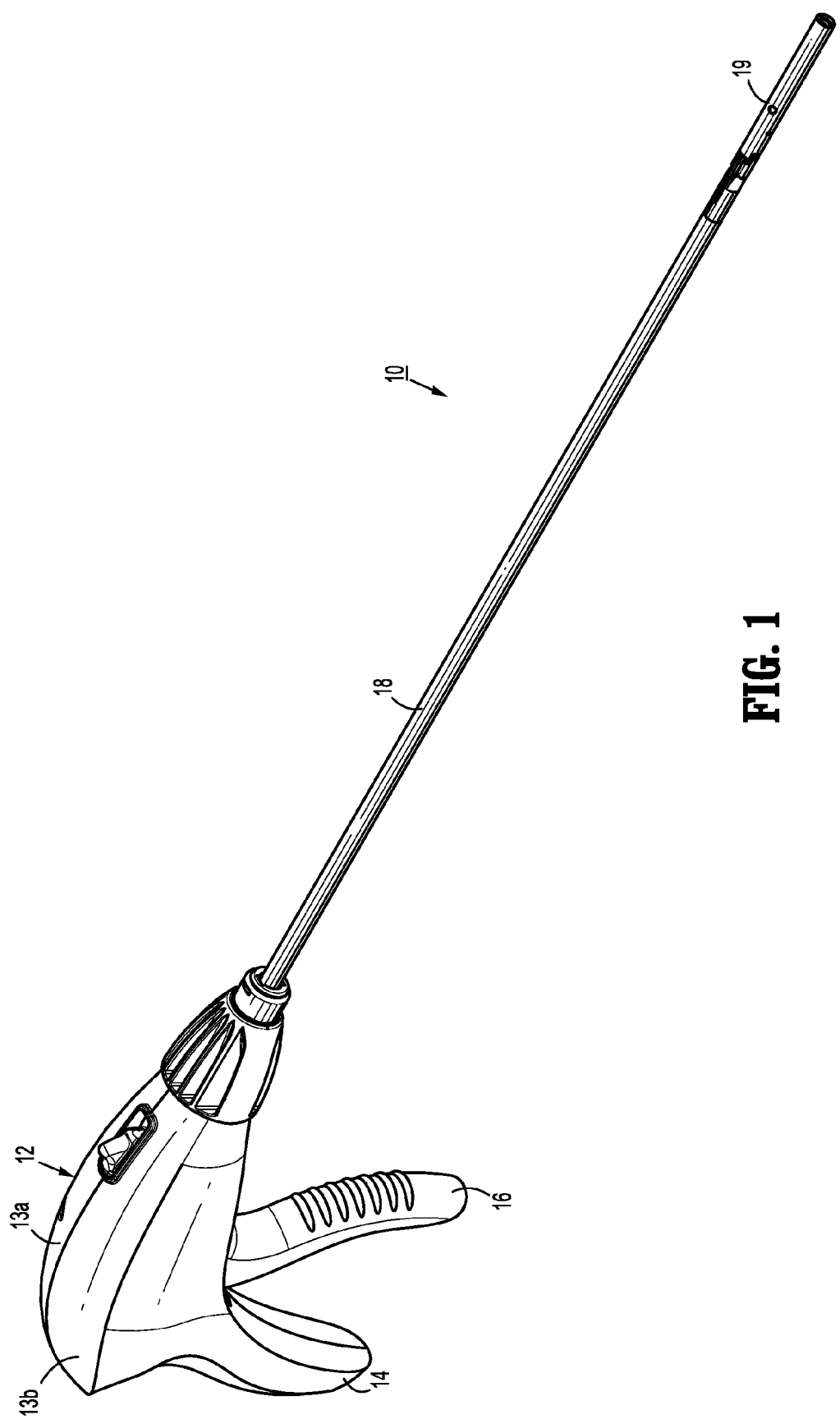
FIG. 1 is a perspective view of one illustrative embodiment of a surgical device provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician.

Figure 2:
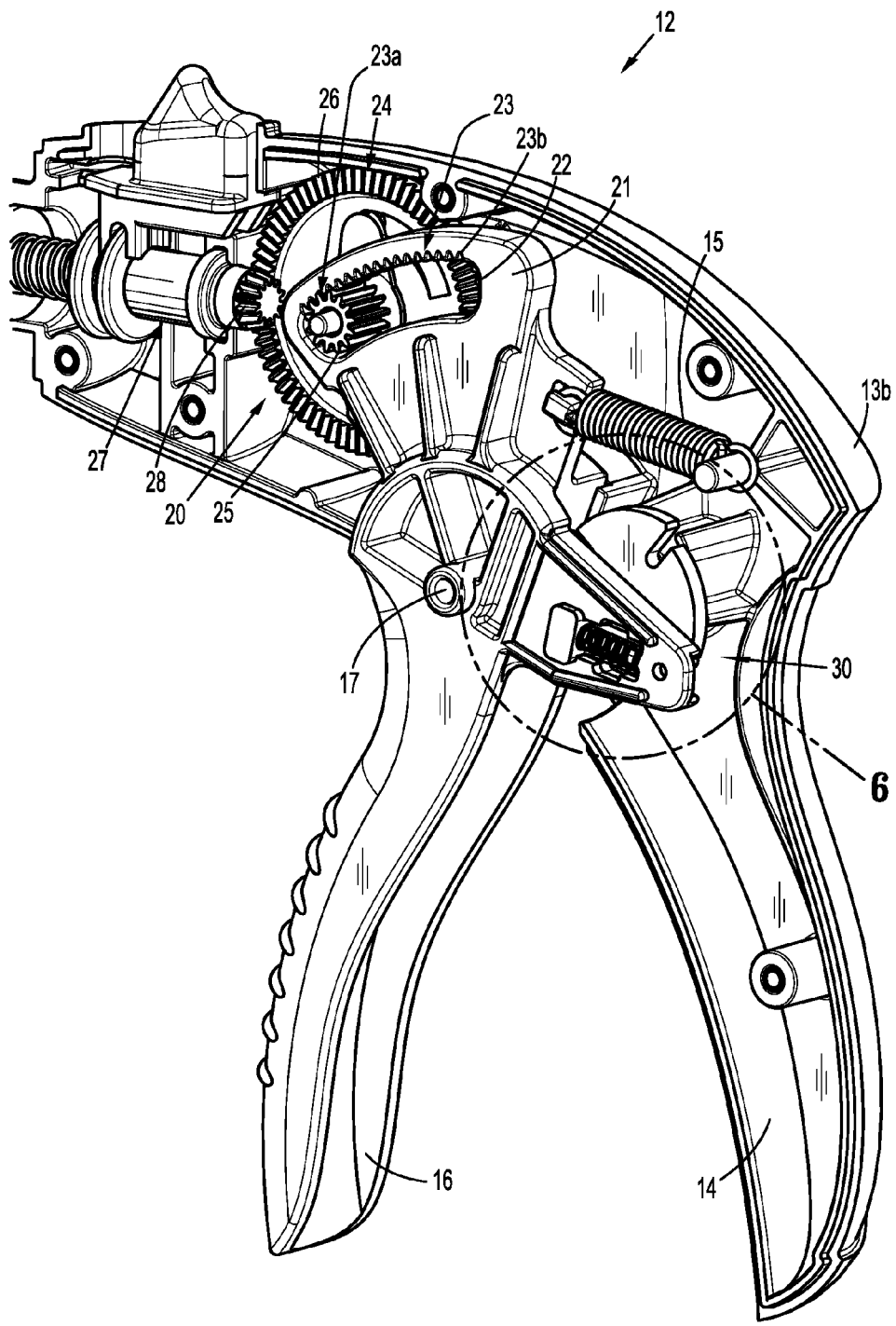
FIG. 2 is a side, perspective view of the surgical device of FIG. 1 with a body shell of a handle assembly removed showing the internal components thereof.

Referring to FIGS. 1 and 2, a surgical device 10 is provided in accordance with the present disclosure including a handle assembly 12, an elongated shaft 18, an end effector 19, a drive assembly 20, and a lockout mechanism 30. Handle assembly 12 includes body shells 13a, 13b, a fixed handle 14, and a moveable handle 16. Body shells 13a, 13b may be joined together by screwing, ultrasonic welding, gluing, or any other known methods of combining parts. Moveable handle 16 is moveable relative to fixed handle 14 wherein moveable handle 16 pivots about a pivot pin 17. A handle biasing member 15 is operatively associated with movable handle 16 to urge movable handle 16 away from fixed handle 14. Elongated shaft 18 extends distally from the handle assembly 12. End effector 19 is removably positioned at the distal end of elongated shaft 18.

Drive assembly 20 is disposed within body shells 13a, 13b of handle assembly 12 and is operatively associated with moveable handle 16 to rotate a driveshaft 27. Drive assembly 20 includes a drive wheel 24 and driveshaft 27. Drive wheel 24 includes a pinion gear 25 and an outer gear 26. Pinion gear 25 may be integrally formed on drive wheel 24. Driveshaft 27 is disposed within elongated shaft 18 (FIG. 1) and is operatively associated with end effector 19 (FIG. 1). Driveshaft 27 includes a bevel or crown gear 28 positioned at a proximal end thereof. Moveable handle 16 includes an internal end 21 that defines an arced opening 22 including a toothed rack 23.

Toothed rack 23 has a first end 23a and a second end 23b. Pinion gear 25 rotatably translates across toothed rack 23 between first and second ends 23a, 23b to rotate drive wheel 24 as moveable handle 16 is moved relative to fixed handle 14. Outer gear 26 cooperates with the rotation of pinion gear 25. Crown gear 28 engages outer gear 26 of drive wheel 24 such that driveshaft 27 cooperates with the rotation of drive wheel 24 to manipulate end effector 19.

As described below, end effector 19 is configured to load and fire fasteners into tissue. As shown, end effector 19 is configured for tack delivery; however, it is contemplated that other end effectors such as staplers, clip appliers, etc. may be used with device 10.

Figure 3:
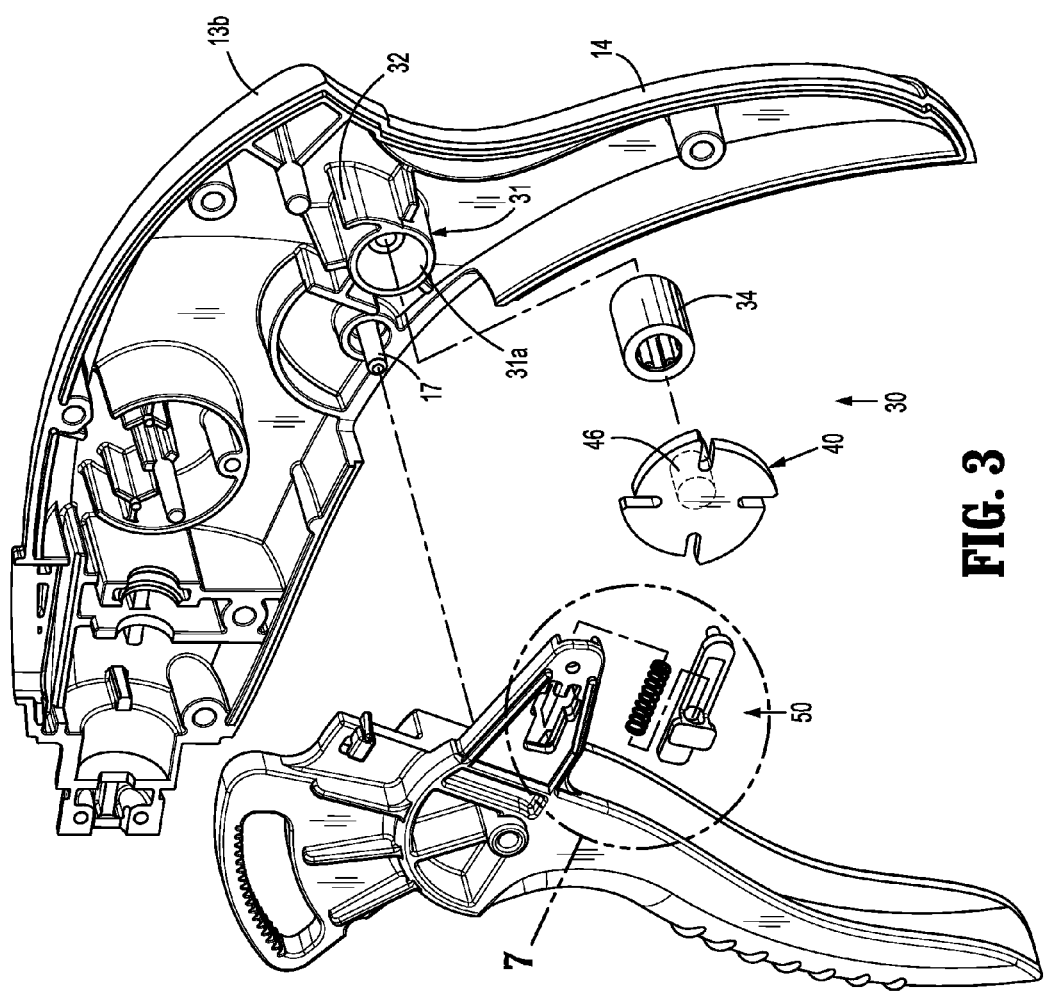
FIG. 3 is a exploded view of internal components of the surgical device of FIG. 1, shown in FIG. 2.
Figure 4:
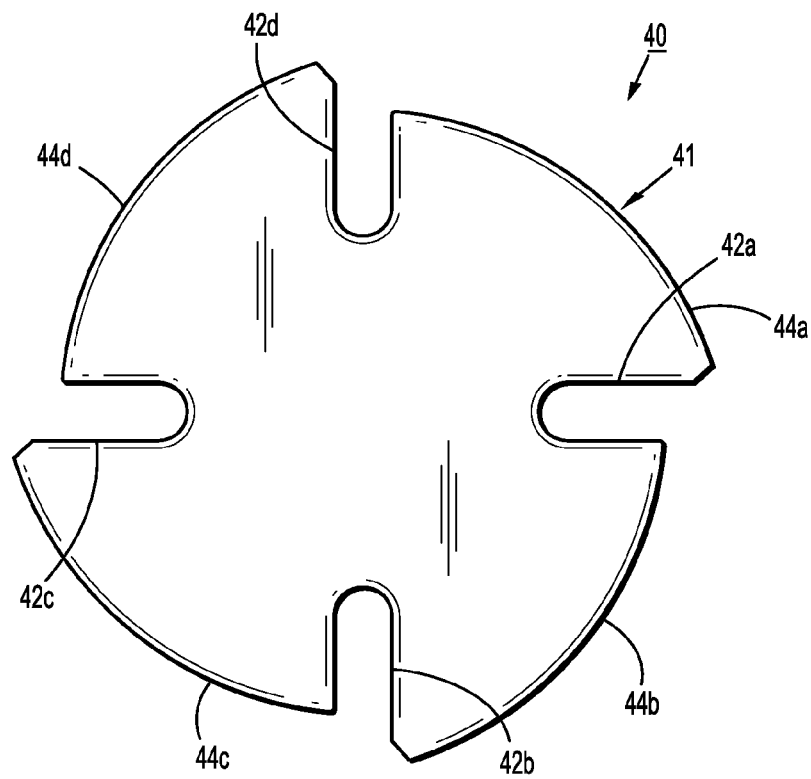
FIG. 4 is plan view of a Geneva wheel shown in FIG. 3.
Figure 5:
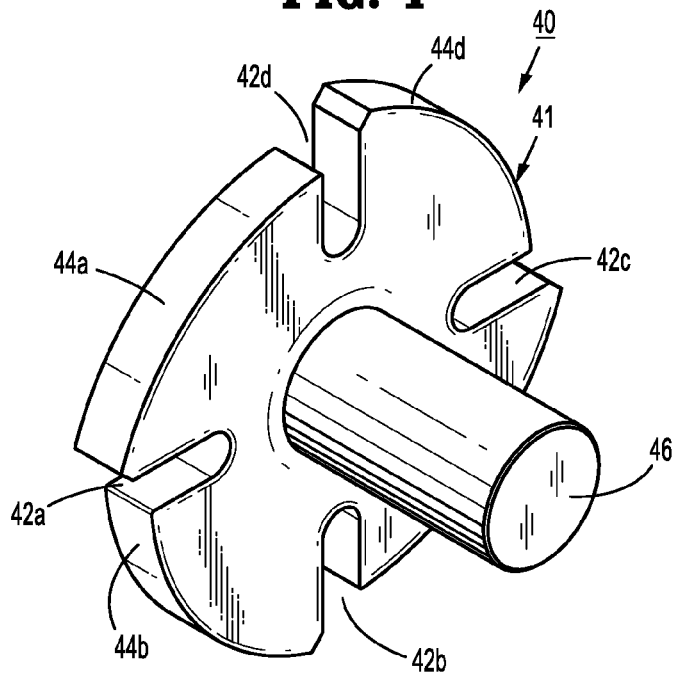
FIG. 5 is a rear, perspective view of the Geneva wheel of FIG. 4.
Figure 6:
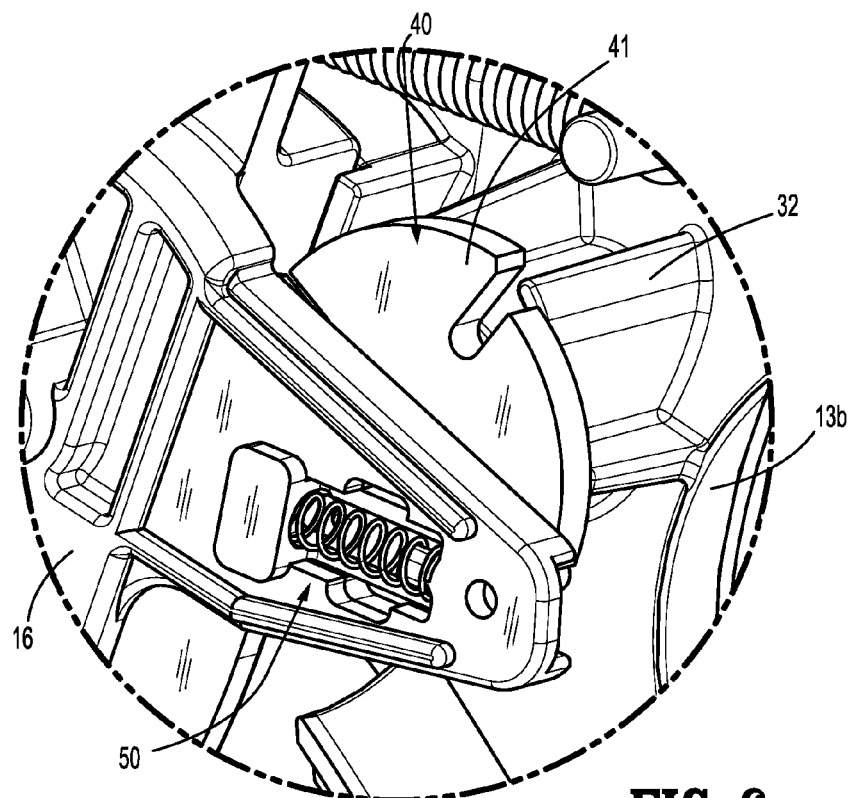
FIG. 6 is an enlarged view of the indicated area of detail of FIG. 2.
Figure 7:
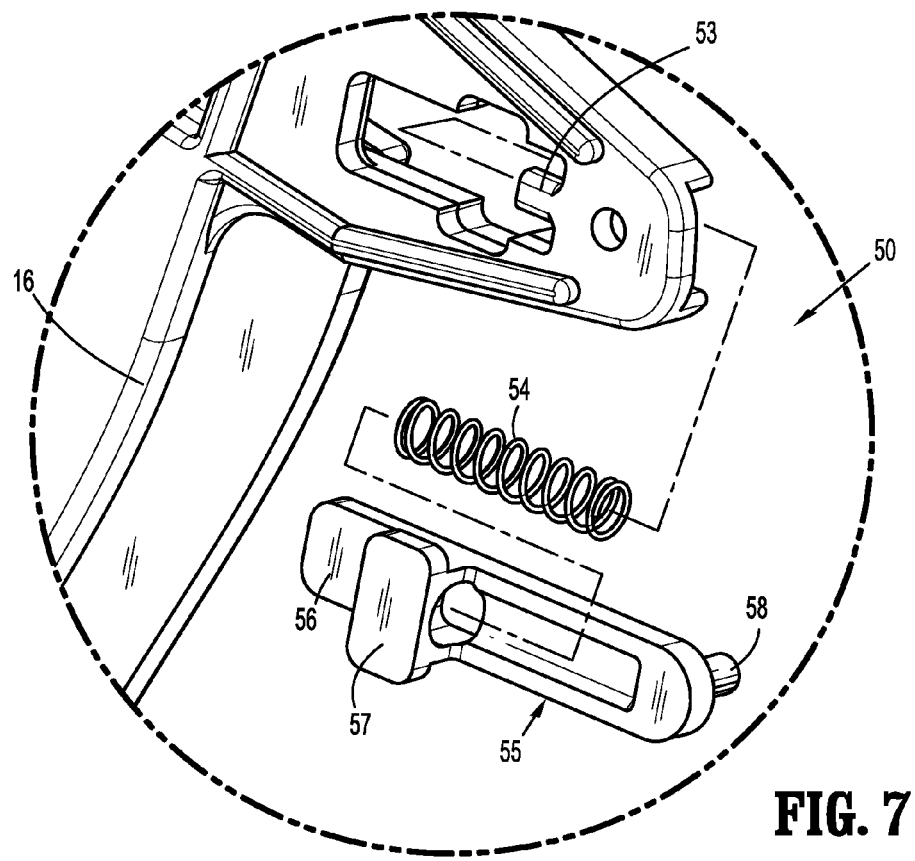
FIG. 7 is an enlarged view of the indicated area of detail of FIG. 3.

Referring to FIGS. 2 and 3, a lockout mechanism 30 is disposed within body shells 13a, 13b of handle assembly 12 and is configured to prevent partial advancement, or rotation of driveshaft 27, or of firing of end effector 19 before reloading, or before permitting moveable handle to return to a fully unactuated or initial position. Lockout mechanism 30 includes a hub 31 defining a cylindrical opening 31a, a ramp 32, a clutch assembly 34, a Geneva wheel 40, and a pin assembly 50. Hub 31 and ramp 32 are integrally formed in body shell 13b.

As can be seen in FIGS. 3-6, Geneva wheel 40 includes a disc portion 41 and a shaft 46 extending therefrom. Disc portion 41 defines slots 42a-d and landings 44a-d. Slots 42a-d are radially spaced equally around disc portion 41. Landings 44a-d are positioned around the periphery of disc portion 41 between slots 42a-d respectively. Shaft 46 is operatively associated with clutch assembly 34 such that clutch assembly 34 permits disc portion 41 to rotate in a first direction (e.g., counter clockwise in FIG. 3) and inhibits rotation of disc portion 41 in an opposite second direction (e.g., clockwise in FIG. 3). As shown, clutch assembly 34 is a roller clutch assembly; however, other clutch assemblies are also envisioned.

With additional reference to FIGS. 6-10, pin assembly 50 is disposed on moveable handle 16 and includes a protrusion 51, a slider biasing member 54, and a slider 55. Protrusion 51 is formed on movable handle 16. In embodiments, protrusion 51 is integrally formed with movable handle 16. Protrusion 51 defines a recess 52 and a support 53. Slider 55 includes a body 56, a retainer 57, and a pin 58. Body 56 of slider 55 is slidably received within recess 52 of protrusion 51.

Pin 58 extends from body 56 and is positioned to engage the periphery of disc 41 of Geneva wheel 40. Pin 58 is sized and configured to be received within slots 41a-d of disc portion 41 of Geneva wheel 40. Slider biasing member 54 is positioned between support 53 of protrusion 51 and retainer 57 of slider 55 and is configured to urge pin 58 into engagement with the periphery of disc portion 41.

Figure 10:
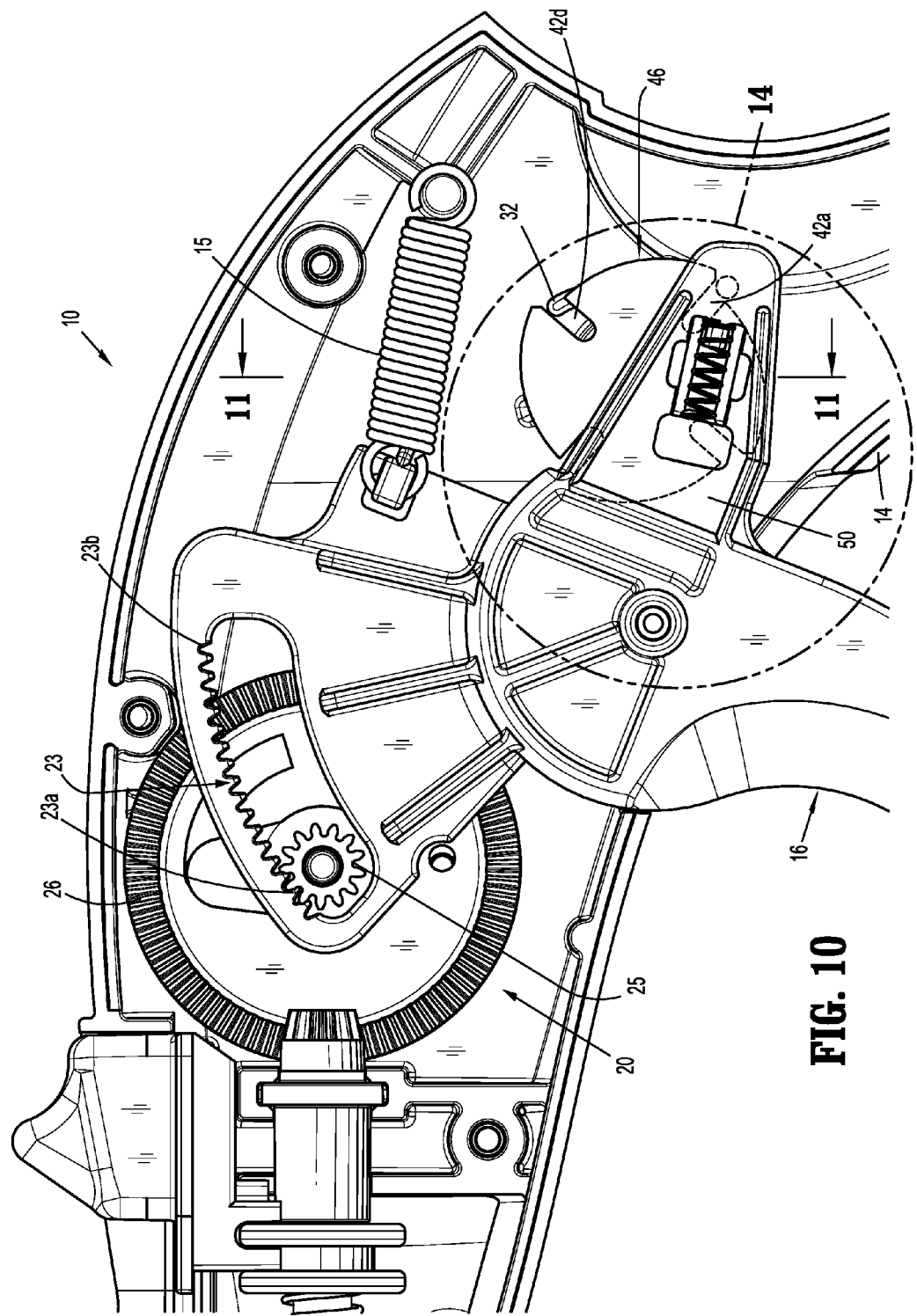
FIG. 10 is an enlarged side, partial view of the surgical device of FIG. 1 with a body shell of the handle assembly removed showing the internal components thereof in an initial or home position.
Figure 13:
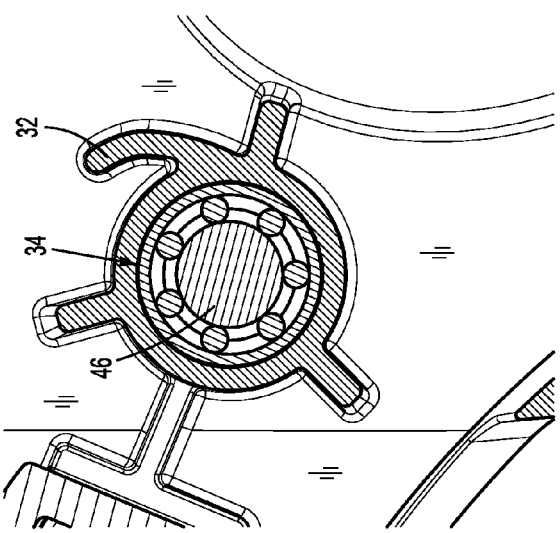
FIG. 13 is rear, cross-sectional view taken along section line "12-12" shown in FIG. 12.
Figure 12:
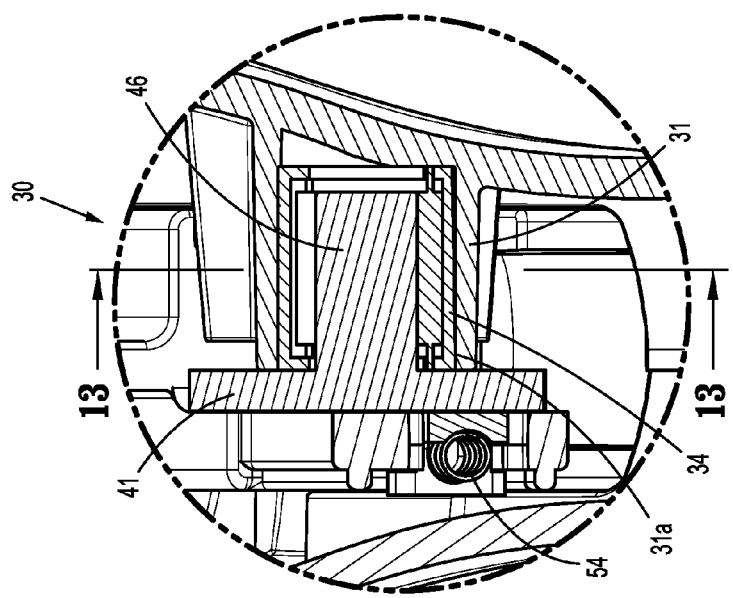
FIG. 12 is an enlarged view of the indicated area of detail of FIG. 11.
Figure 11:
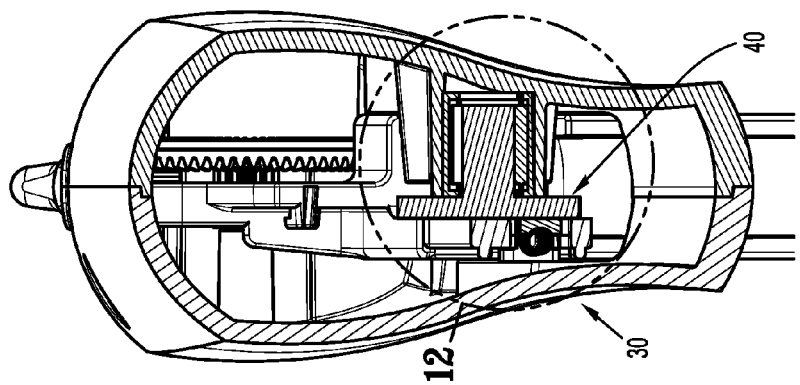
FIG. 11 is rear, cross-sectional view taken along section line "11-11" shown in FIG. 10.
Figure 14:
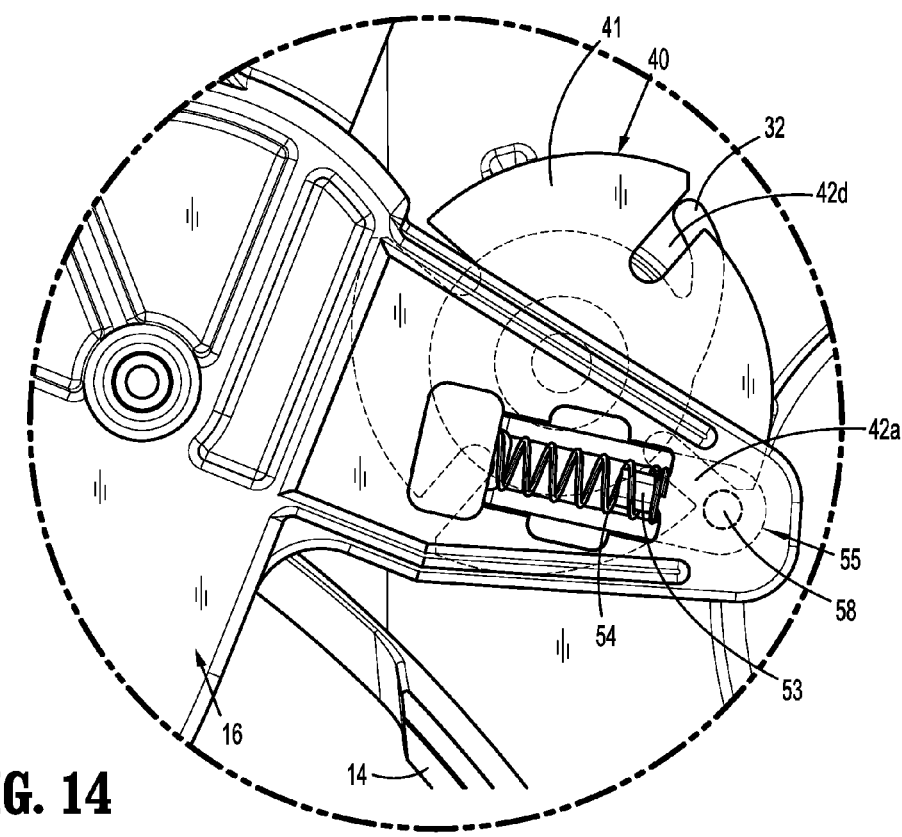
FIGS. 14-19 are enlarged sequential operational views of the indicated areas of detail of FIG. 10 progressing from the initial position through a full-squeeze and a return stroke of the surgical device.

Referring to FIG. 10, surgical device 10 fires fasteners from end effector 19 (FIG. 1) into tissue as moveable handle 16 moves from an initial or home position to a compressed or full-squeezed position, and advances a stack of fasteners of end effector 19 as moveable handle 16 moves through a complete stroke (complete squeeze and release of movable handle 16). Each full-squeeze of moveable handle 16 engages pinion gear 25 from a first end 23a of toothed rack 23 to a second end 23b of toothed rack 23 to rotate outer gear 26 which rotates crown gear 28. Crown gear 28 rotates driveshaft 27 to fire a fastener from end effector 19 as movable handle 16 reaches the full-squeezed position. As moveable handle 16 returns from the full-squeezed position to the initial or home position, the rotation of driveshaft 27 continues to engage end effector 19 to advance the stack of fasteners of end effector 19 by an amount such that the next distal-most fastener is ready to be fired with the next full squeeze of moveable handle 16.

Referring to FIGS. 10-19, the cycling of moveable handle 16 from the initial or home position to the full-squeezed position and returning to the initial or home position is described in detail. Each cycle of the moveable handle may represent the firing of a fastener, e.g., surgical tack, staple, clip, etc., to join two portions of tissue, seal the end of a vessel by the end effector, apply a surgical mesh to a target site, or to tack down body tissue. End effector 19 may include a plurality of fasteners arranged in a stack. In use, each cycle of the moveable handle 16, from the initial or home portion to the full-squeezed position and returning to the initial or home position, fires a distal-most fastener and loads or advances the next fastener into a firing position within the end effector 19 for the next cycle of moveable handle 16.

With reference to FIGS. 10-14, moveable handle 16 is in an uncompressed position, initial, or home position spaced-apart from fixed handle 14. Pinion gear 25 is positioned at a first end 23a of toothed rack 23. Geneva wheel 40 is aligned such that one of slots 42a-d (e.g., slot 42d) is aligned with the end of ramp 32 and an adjacent slot 42a-d (e.g., slot 42a) is engaged with pin 58 of slider 55.

Figure 15:
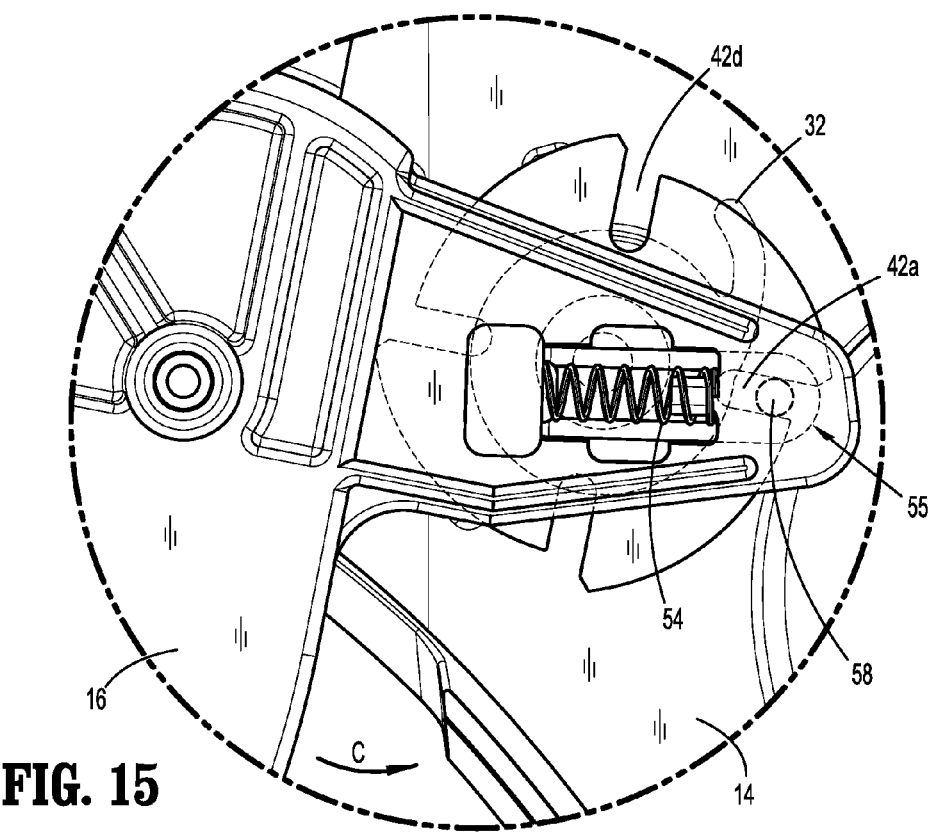

Referring to FIG. 15, moveable handle 16 is compressed or moved toward fixed handle 14 as represented by arrow "C." As moveable handle 16 is compressed, pin 58 engages slot 42a to rotate Geneva wheel 40 in a first direction (i.e., counter-clockwise as shown in FIG. 15). As Geneva wheel 40 rotates, slider biasing member 54 urges pin 58 to slide towards the center of disc portion 41 within slot 42a. Clutch assembly 34 permits rotation of Geneva wheel 40 in the first direction and engages shaft 46 of Geneva wheel 40 to inhibit Geneva wheel 40 from rotating in an opposite second direction (i.e., clockwise as shown in FIG. 15). By inhibiting Geneva wheel 40 from rotating in the second direction, slot 42a engages pin 58 to restrict moveable handle 16 from moving away from fixed handle 14.

Figure 16:
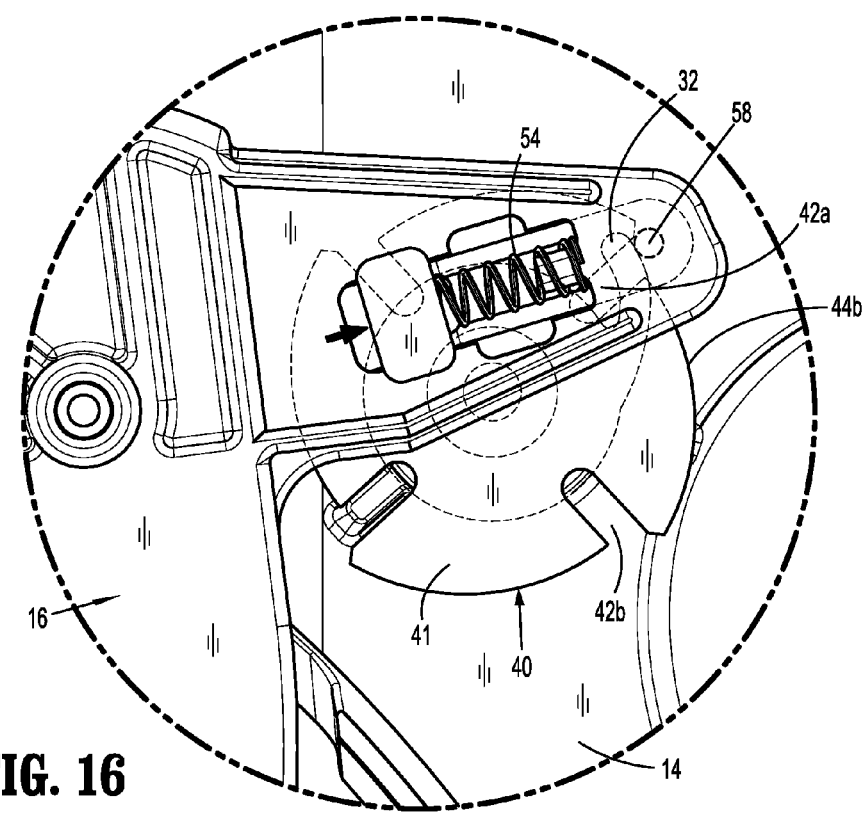

Referring now to FIG. 16, continued compression of moveable handle 16 towards fixed handle 14 completes a full-squeeze of surgical device 10 such that moveable handle 16 is in a full-squeezed position with slot 42a of Geneva wheel 40 aligned with the end of ramp 32. Pin 58 is engaged within slot 42a and with ramp 32 such that ramp 32 engages pin 58 to move slider 55 against slider biasing member 54 to move pin 58 from within slot 42a beyond landing 44b. Clutch assembly 34 continues to engage shaft 46 of Geneva wheel 40 to inhibit rotation of Geneva wheel 40 in the second direction.

Figure 17:
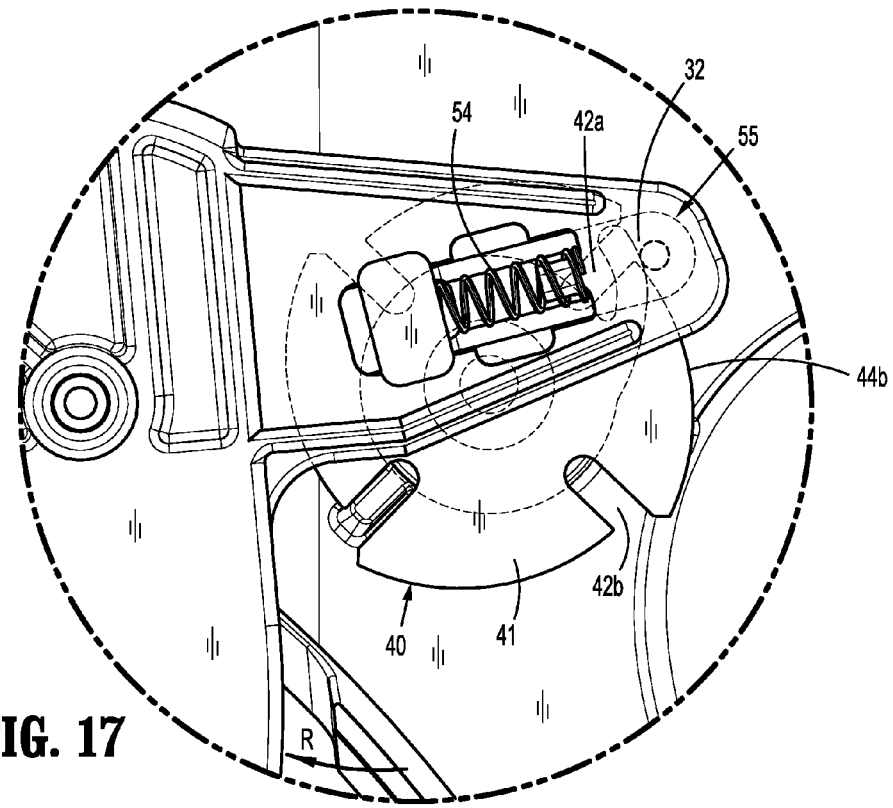

With reference to FIG. 17, once surgical device 10 completes a full squeeze of movable handle 16, further movement of moveable handle 16 towards fixed handle 14 is inhibited. Further movement of moveable handle 16 may be inhibited by interference or abutment of fixed handle 14 and movable handle 16. In embodiments, further movement of moveable handle 16 is inhibited by pinion 25 engaging a second end 23b of toothed rack 23 (FIG. 10).

With continued reference to FIG. 17, moveable handle 16 is returned to the initial or home position by moving away from fixed handle 14, as indicated by arrow "R." In embodiments, handle biasing member 15 (FIG. 10) urges or helps to urge moveable handle 16 away from fixed handle 14. As moveable handle 16 returns to the initial position, pin 58 slides down ramp 32 and into engagement with landing 44b of disc portion 41. It will be appreciated that slider biasing member 54 maintains pin 58 in engagement with ramp 32 or landing 44b of Geneva wheel 40.

Figure 18:
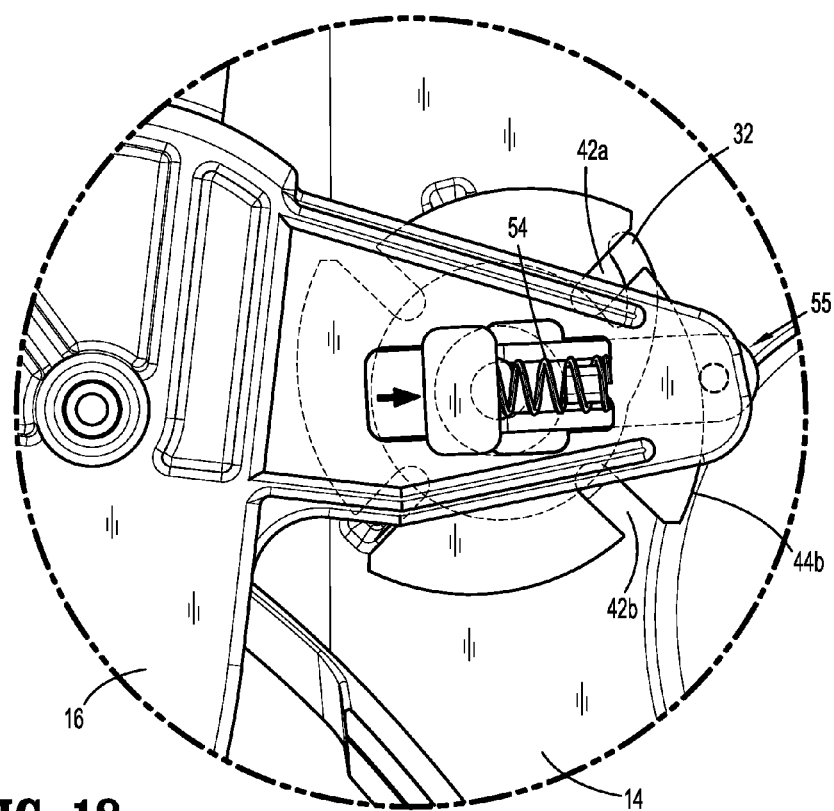

Referring now to FIG. 18, continued movement or opening of movable handle 16, slides pin 58 along landing 44b of disc portion 41. As pin 58 slides along landing 44b, landing 44b engages pin 58 to move slider 55 against slider biasing member 54. In embodiments, handle biasing member 15 overcomes the force of slider biasing member 54 to automatically or to help return moveable handle 16 to the initial or home position. In some embodiments, moveable handle 16 requires manual force to return handle 16 to the initial or home position.

Figure 19:
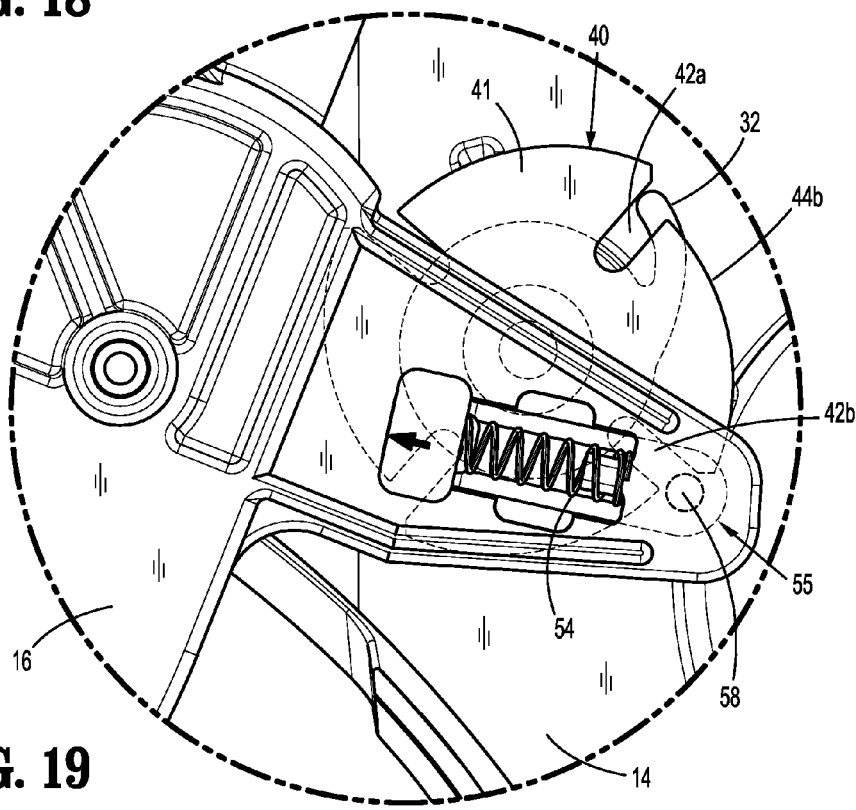

Referring to FIG. 19, moveable handle 16 is shown returned to the initial or home position. As illustrated in FIG. 19, pin 58 has slid off landing 44b and into engagement with slot 42b. Additionally, slider biasing member 54 has urged slider towards the center of disc portion 41 to move pin 58 within and into engagement with slot 42b. In embodiments, pinion gear 25 has engaged first end 23a of toothed rack 23 to restrict further movement of moveable handle 16 away from fixed handle 14. In some embodiments, pin 58 engages slot 42b to restrict further movement of moveable handle 16 away from fixed handle 14.

It will be appreciated that during the return portion of the stroke, i.e., from the full-squeezed position back to the initial or home position, clutch assembly 34 engages shaft 46 of Geneva wheel 40 to inhibit rotation of Geneva wheel 40 in the second direction. During the return stroke, Geneva wheel 40 may be inhibited from rotation in the first direction by the internal friction of the components of surgical device 10.

When moveable handle 16 is returned to the initial or home position, surgical device 10 is ready for a second firing or cycle. Each successive cycle of moveable handle 16 from the initial or home position to the full-squeezed position and returning to the initial or home position advances Geneva wheel 40 one-quarter rotation or 90° such that the next slot 42a-d engages pin 58 as pin 58 slides down the next successive landing 44a-d. It is also contemplated that a Geneva wheel may be provided including more or less slots and that the rotation of each cycle may include less than or more than one-quarter rotation.

Figure 20:
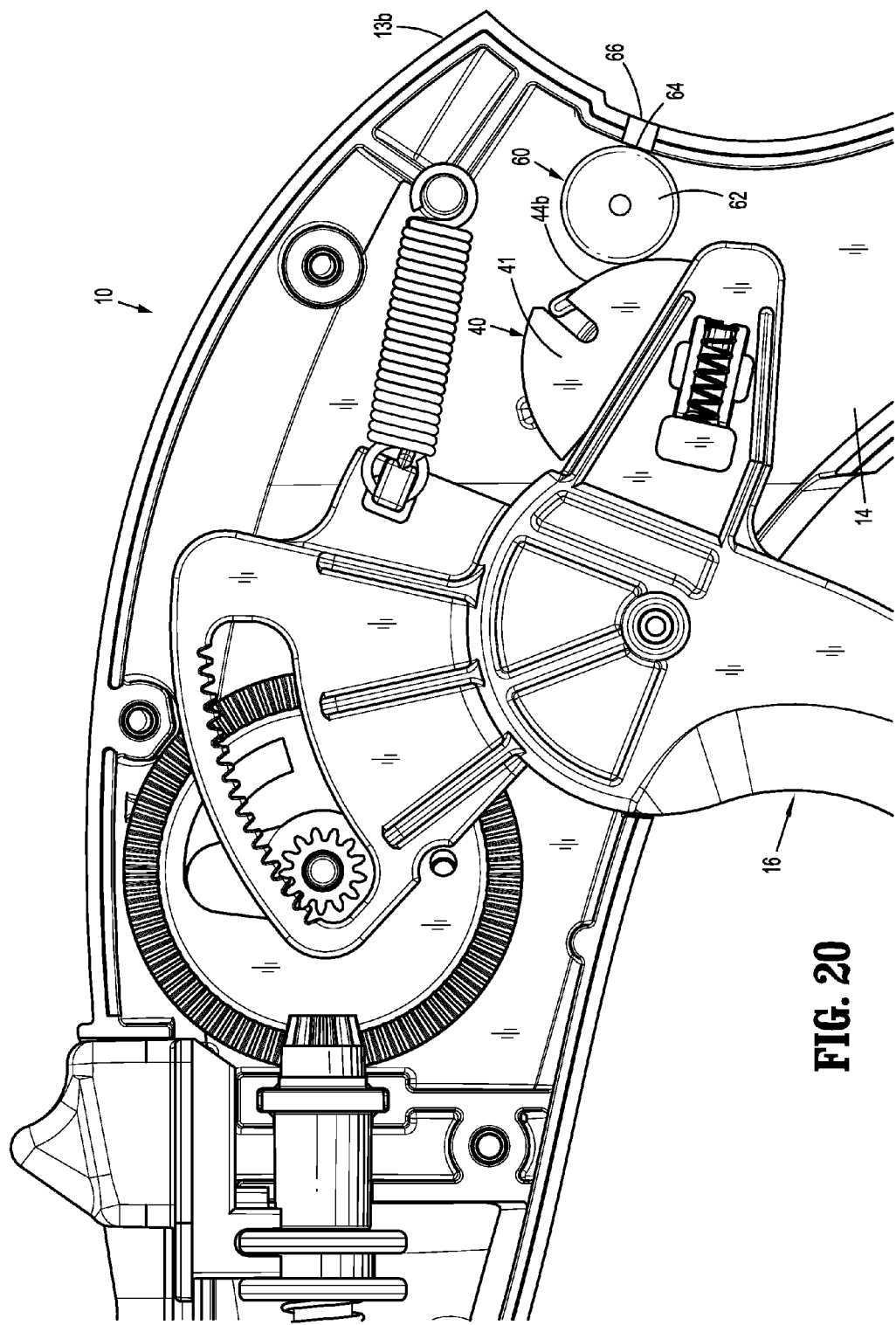
FIG. 20 is an enlarged, partial side view of the surgical device of FIG. 1 with a body shell of the handle assembly removed showing the internal components including a counter mechanism driven by the Geneva wheel.

Referring to FIG. 20, surgical device 10 includes a counter mechanism 60 configured to provide indicia of the number complete or full of cycles of moveable handle 16. Counter mechanism 60 includes a wheel 62 and indicia 64 provided thereon. Wheel 62 engages landings 44a-d of Geneva wheel 40 as Geneva wheel 40 rotates in the first direction. Each cycle or complete stroke of moveable handle advances wheel 62 to increase indicia 64 by one unit. Wheel 62 may be positioned to engage landings 44a-d of Geneva wheel 40 without interfering with pin 58. Indicia 64 may be disposed on the outer periphery of wheel 62 and may be visible through an opening 66 in body shells 13a, 13b in the rear of surgical device 10. Other locations for indicia 64 and opening 66 are also contemplated.

Figure 23:
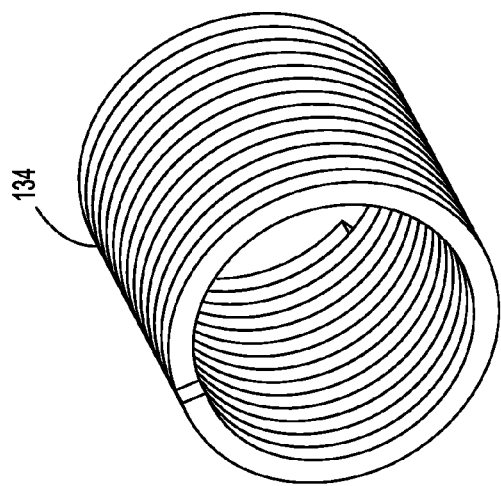
FIG. 23 is a perspective view of the spring wrap clutch of FIG. 21.
Figure 22:
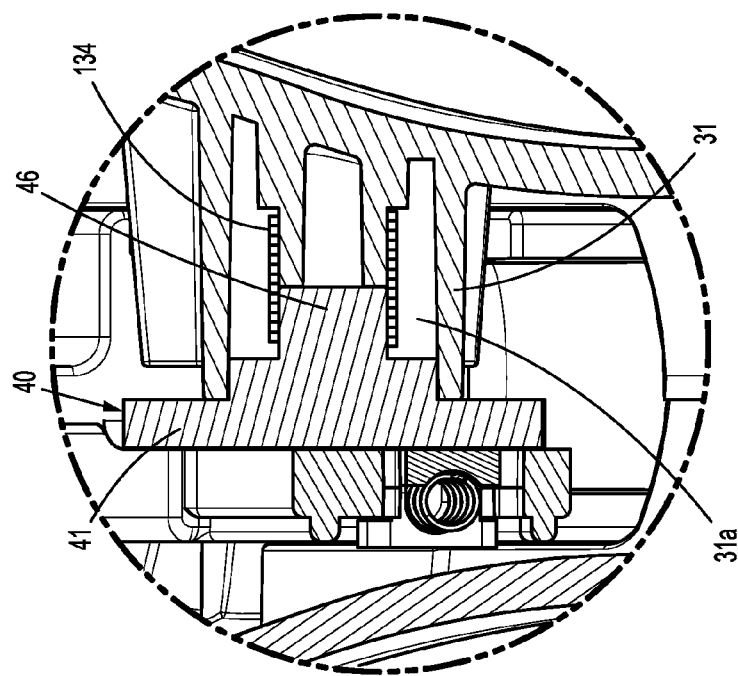
FIG. 22 is an enlarged view of the indicated area of detail of FIG. 21.
Figure 21:
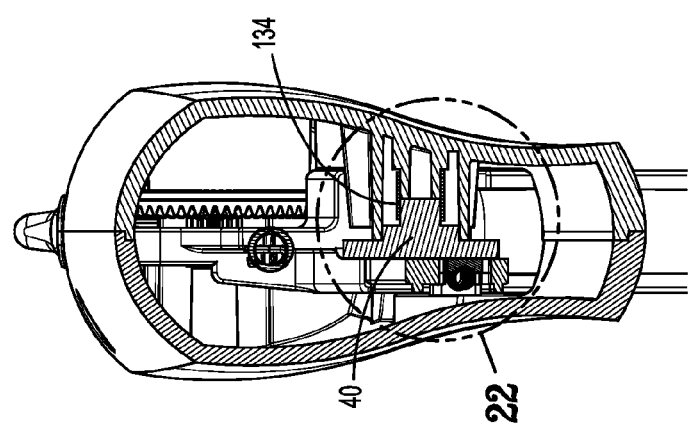
FIG. 21 is rear cross-sectional view of another illustrative clutch assembly in accordance with the present disclosure including a spring wrap clutch.

Referring to FIGS. 21-23, another clutch assembly 134 is provided in accordance with the present disclosure. Clutch assembly 134 may be used with surgical device 10 as an alternative to clutch assembly 34 described above. Clutch assembly 134 is positioned within opening 31 around and in engagement with shaft 46 of Geneva wheel 40. The function of clutch assembly 134 within surgical device 10 is substantially similar to clutch assembly 34 engaging shaft 46 of Geneva wheel 40 to permit rotation in the first direction and inhibit rotation in the opposite second direction. Clutch assembly 134 is in the form of a spring wrap clutch that is coiled around and in engagement with shaft 46 of Geneva wheel 40 such that rotation in the first direction expands the spring wrap permitting rotation of Geneva wheel 40 and rotation in the second direction compresses the spring wrap against shaft 46 inhibiting rotation of Geneva wheel 40.

While several embodiments of the disclosure have been shown in the drawings and described herein, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A surgical device comprising:
   a handle assembly including a fixed handle and a moveable handle, the moveable handle including an internal end defining an opening, the opening including a toothed rack, the moveable handle having an initial position, wherein the moveable handle is spaced-apart from the fixed handle, and a full-squeezed position, wherein the moveable handle is approximated toward the fixed handle;
   an elongated member extending from the handle assembly and defining a longitudinal axis;
   an end effector positioned at a distal end of the elongated member;
   a drive assembly disposed within the handle assembly and engaged by the toothed rack of the moveable handle to transmit a rotative force to manipulate the end effector; and
   a lockout mechanism disposed within the handle assembly and engaged with the moveable handle to prevent movement of the moveable handle towards the initial position before the moveable handle reaches the full-squeezed position, the lockout mechanism including a wheel and a clutch, wherein the wheel rotates in a first direction as the moveable handle is moved towards the full-squeezed position, and wherein the clutch engages the wheel and permits the wheel to rotate in the first direction and the clutch inhibits the wheel from rotating in a second direction opposite the first direction.

2. The surgical device of claim 1, wherein the lockout mechanism further includes a slider having a pin and the wheel defines a plurality of slots, the plurality of slots extending from the outer periphery of the wheel towards a center of the wheel, the pin engaging one of the plurality of slots to rotate the wheel in the first direction when the moveable handle is moved towards the full-squeezed position, the pin engaged by one of the plurality of slots to prevent the moveable handle from moving towards the initial position before the moveable handle reaches the full-squeezed position.

3. The surgical device of claim 2, further comprising a slider biasing member urging the slider such that the pin engages the periphery of the wheel, the pin sliding within one of the plurality of slots when the moveable handle is moved from the initial position to the full-squeezed position.

4. The surgical device of claim 3, wherein the handle assembly includes a ramp formed therein, the ramp positioned to move the pin against the slider biasing member from within one of the plurality of slots of the wheel when the moveable handle reaches the full-squeezed position.

5. The surgical device of claim 4, wherein the wheel includes a plurality of landings positioned about a periphery thereof, each of the plurality of landings positioned between a respective two of the plurality of slots, the pin engaging one of the plurality of landings as the moveable handle returns from the full-squeezed position to the initial position.

6. The surgical device of claim 5, wherein when the moveable handle returns to the initial position the pin engages another of the plurality of slots adjacent to the one of the plurality of slots about the wheel.

7. The surgical device of claim 1, wherein the clutch includes a roller clutch.

8. The surgical device of claim 1, wherein the clutch includes a spring wrap clutch.

9. A surgical device comprising:
   a handle assembly including a fixed handle and a moveable handle, the moveable handle including an internal end defining an opening, the opening including a toothed rack, the moveable handle having an initial position, wherein the moveable handle is spaced-apart from the fixed handle, and a full-squeezed position, wherein the moveable handle is approximated toward the fixed handle;

a drive assembly disposed within the handle assembly and engaged by the toothed rack of the moveable handle; wherein the drive assembly is configured to engage a driveshaft and transmit a rotative force thereto; and a lockout mechanism disposed within the handle assembly and engaged with the moveable handle to prevent movement of the moveable handle towards the initial position before the moveable handle reaches the full-squeezed position, the lockout mechanism including a wheel and a clutch, wherein the wheel rotates in a first direction as the moveable handle is moved towards the full-squeezed position, and wherein the clutch engages the wheel and permits the wheel to rotate in the first direction and the clutch inhibits the wheel from rotating in a second direction opposite the first direction.

10. The surgical device of claim 9, wherein the lockout mechanism further includes a slider having a pin and the wheel defines a plurality of slots, the plurality of slots extending from the outer periphery of the wheel towards a center of the wheel, the pin engaging one of the plurality of slots to rotate the wheel in the first direction when the moveable handle is moved towards the full-squeezed position, the pin engaged by one of the plurality of slots to prevent the moveable handle from moving towards the initial position before the moveable handle reaches the full-squeezed position.

11. The surgical device of claim 10, further comprising a slider biasing member urging the slider such that the pin engages the periphery of the wheel, the pin sliding within one of the plurality of slots when the moveable handle is moved from the initial position to the full-squeezed position.

12. The surgical device of claim 11, wherein the handle assembly includes a ramp formed therein, the ramp positioned to move the pin against the slider biasing member from within one of the plurality of slots of the wheel when the moveable handle reaches the full-squeezed position.

13. The surgical device of claim 12, wherein the wheel includes a plurality of landings positioned about a periphery thereof, each of the plurality of landings positioned between a respective two of the plurality of slots, the pin engaging one of the plurality of landings as the moveable handle returns from the full-squeezed position to the initial position.

14. The surgical device of claim 13, wherein when the moveable handle returns to the initial position the pin engages another of the plurality of slots adjacent to the one of the plurality of slots about the wheel.

* * * * *